United States Patent
Shaga et al.

(10) Patent No.: US 12,197,694 B2
(45) Date of Patent: Jan. 14, 2025

(54) CORRECTING FOR EMITTED LIGHT WAVELENGTH VARIATION IN BLOOD-OXYGEN SATURATION MEASUREMENTS AT WEARABLE ELECTRONIC DEVICE

(71) Applicant: Apple Inc., Cupertino, CA (US)

(72) Inventors: Ravi K. Shaga, Sunnyvale, CA (US); Paul D. Mannheimer, Los Altos, CA (US); Theodore Yu, San Jose, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 18/215,694

(22) Filed: Jun. 28, 2023

(65) Prior Publication Data

US 2023/0341991 A1 Oct. 26, 2023

Related U.S. Application Data

(63) Continuation of application No. 17/018,985, filed on Sep. 11, 2020, now Pat. No. 11,723,563.

(51) Int. Cl.
*G06F 3/04815* (2022.01)
*G06F 3/03* (2006.01)
(Continued)

(52) U.S. Cl.
CPC ........ *G06F 3/04815* (2013.01); *G06F 3/0304* (2013.01); *G06F 3/0484* (2013.01);
(Continued)

(58) Field of Classification Search
CPC . A61B 5/14552; A61B 5/1455; A61B 5/1495; A61B 5/681; A61B 5/7203;
(Continued)

(56) References Cited

U.S. PATENT DOCUMENTS

| 4,913,150 A | 4/1990 | Cheung et al. |
| 6,313,612 B1 | 11/2001 | Honda |

(Continued)

FOREIGN PATENT DOCUMENTS

| CN | 103876726 | 6/2014 |
| CN | 203943664 | 11/2014 |

(Continued)

*Primary Examiner* — Eric F Winakur
*Assistant Examiner* — Abid A Mustansir
(74) *Attorney, Agent, or Firm* — Brownstein Hyatt Farber Schreck, LLP

(57) ABSTRACT

A measurement engine of a wearable electronic device may compensate for wavelength variations of light emitted as part of blood-oxygen saturation measurements. In some cases, determining an estimated blood-oxygen saturation value is based at least partially on temperature data that may be used to compensate for temperature-based wavelength variations of the emitted light, drive current data that may be used to compensate for drive-current-based wavelength variations of the emitted light, and/or calibration information that may be used to compensate for manufacturing variability across different light emitters. In various embodiments, the measurement engine may use temperature data, the drive current data, and/or calibration information in a variety of ways to determine estimated blood-oxygen saturation values, including using lookup tables or calibration curves, applying functions, and the like.

20 Claims, 11 Drawing Sheets

(51) Int. Cl.
*G06F 3/048* (2013.01)
*G06F 3/0482* (2013.01)
*G06F 3/0484* (2022.01)
*G06T 7/13* (2017.01)
*G06T 7/55* (2017.01)
*G06T 7/62* (2017.01)
*G06T 11/20* (2006.01)
*G06T 13/00* (2011.01)
*G06T 19/00* (2011.01)
*G06T 19/20* (2011.01)
*G06V 20/20* (2022.01)

(52) U.S. Cl.
CPC .......... *G06T 7/13* (2017.01); *G06T 7/55* (2017.01); *G06T 7/62* (2017.01); *G06T 11/203* (2013.01); *G06T 13/00* (2013.01); *G06T 19/006* (2013.01); *G06T 19/20* (2013.01); *G06V 20/20* (2022.01); *G06F 3/048* (2013.01); *G06F 3/0482* (2013.01); *G06T 2200/24* (2013.01); *G06T 2219/004* (2013.01); *G06T 2219/2004* (2013.01)

(58) Field of Classification Search
CPC .... A61B 2562/0238; A61B 2562/0271; A61B 2562/043; A61B 2562/046; A61B 2560/0252; A61B 2562/0233; G01K 13/00

See application file for complete search history.

(56) References Cited

U.S. PATENT DOCUMENTS

| | | | |
|---|---|---|---|
| 6,526,300 B1 | 2/2003 | Kiani et al. |
| 6,662,033 B2 | 12/2003 | Casciani et al. |
| 6,882,874 B2 | 4/2005 | Huiku |
| 7,206,621 B2 | 4/2007 | Aoyagi et al. |
| 8,463,345 B2 | 6/2013 | Kuhn et al. |
| 8,948,832 B2 | 2/2015 | Hong et al. |
| 9,226,663 B2 | 1/2016 | Fei |
| 9,558,336 B2 | 1/2017 | Lee |
| 9,597,014 B2 | 3/2017 | Venkatraman et al. |
| 9,743,838 B2 | 8/2017 | Richards |
| 9,763,607 B1 | 9/2017 | Acosta et al. |
| 10,032,557 B1 | 7/2018 | Bossetti |
| 10,092,197 B2 | 10/2018 | Han |
| 10,117,587 B2 | 11/2018 | Han |
| 10,165,954 B2 | 1/2019 | Lee |
| 10,178,959 B1 | 1/2019 | Homyk |
| 10,181,021 B2 | 1/2019 | Verkatraman et al. |
| 10,188,330 B1 | 1/2019 | Kadlec et al. |
| 10,241,476 B1 | 3/2019 | Moten |
| 10,278,592 B2 | 5/2019 | Fish et al. |
| 10,417,513 B2 | 9/2019 | Lee |
| 10,433,739 B2 | 10/2019 | Weekly et al. |
| 10,444,067 B2 | 10/2019 | Hsu et al. |
| 10,485,437 B2 | 11/2019 | Wei et al. |
| 10,485,478 B1 | 11/2019 | Mirov |
| 10,537,270 B2 | 1/2020 | Sarussi et al. |
| 10,586,525 B1 | 2/2020 | Wu et al. |
| 10,627,783 B2 | 4/2020 | Rothkopf |
| 10,646,145 B2 | 5/2020 | Pekander et al. |
| 10,687,718 B2 | 6/2020 | Allec et al. |
| 10,702,211 B2 | 7/2020 | Clavelle et al. |
| 10,732,574 B2 | 8/2020 | Shim et al. |
| 10,736,552 B2 | 8/2020 | Ferber et al. |
| 10,760,955 B2 | 9/2020 | Chu et al. |
| 10,918,322 B2 | 2/2021 | Shao |
| 10,966,643 B1 | 5/2021 | Vavadi |
| 11,018,524 B2 | 5/2021 | Simpson |
| 11,076,769 B2 | 8/2021 | Lee |
| 11,145,310 B2 | 10/2021 | Sakurai |
| 11,224,381 B2 | 1/2022 | McHale et al. |
| 11,573,351 B2 | 2/2023 | Mehra et al. |
| 11,717,197 B2 | 8/2023 | Venugopal et al. |
| 11,723,563 B1 | 8/2023 | Shaga et al. |
| 2003/0176776 A1* | 9/2003 | Huiku ............... A61B 5/1495 600/322 |
| 2015/0054348 A1 | 2/2015 | Akiya |
| 2015/0099943 A1 | 4/2015 | Russell |
| 2016/0129279 A1 | 5/2016 | Ferolito |
| 2016/0278712 A1 | 9/2016 | Sagara |
| 2017/0095216 A1 | 4/2017 | Laty |
| 2017/0135633 A1 | 5/2017 | Connor |
| 2017/0172476 A1 | 6/2017 | Schilthuizen |
| 2017/0251963 A1 | 9/2017 | Hashimoto et al. |
| 2018/0344175 A1 | 12/2018 | Rulkov et al. |
| 2019/0072912 A1 | 3/2019 | Pandya et al. |
| 2019/0090766 A1 | 3/2019 | Block et al. |
| 2019/0090806 A1 | 3/2019 | Clavelle et al. |
| 2019/0167124 A1 | 6/2019 | Verkruijsse et al. |
| 2020/0163616 A1 | 5/2020 | Sakaya |
| 2022/0085231 A1 | 3/2022 | Liu et al. |
| 2023/0341991 A1 | 10/2023 | Shaga et al. |

FOREIGN PATENT DOCUMENTS

| | | |
|---|---|---|
| CN | 109589095 | 4/2019 |
| CN | 109645972 | 4/2019 |
| EP | 3451117 | 3/2019 |
| KR | 20180042472 | 4/2018 |

* cited by examiner

CORRECTING FOR EMITTED LIGHT WAVELENGTH VARIATION IN BLOOD-OXYGEN SATURATION MEASUREMENTS AT WEARABLE ELECTRONIC DEVICE

CROSS-REFERENCE TO RELATED APPLICATION

This application is a continuation of U.S. patent application Ser. No. 17/018,985, filed Sep. 11, 2020, the contents of which are incorporated herein by reference as if fully disclosed herein.

FIELD

Embodiments relate generally to sensing blood-oxygen saturation using a wearable electronic device. More particularly, the described embodiments relate to methods and systems for compensating for variations in the wavelength of light emitted by a wearable electronic device across different devices and in different operating conditions to achieve reliable blood-oxygen saturation measurements.

BACKGROUND

In some cases, performing optical blood-oxygen saturation measurements includes emitting first-colored light and second-colored light toward a user. For each of the first-colored light and the second-colored light, a light sensor may detect a signal corresponding to a portion of the light that has interacted with the user. A processor may determine the amplitudes of pulsatile components and non-pulsatile components of the signals, and may determine a modulation amplitude corresponding to each signal by dividing an amplitude of the pulsatile component of the signal by an amplitude of the non-pulsatile component of the signal.

The processor may determine a modulation ratio by dividing the modulation amplitude of the signal corresponding to the first-colored light by the modulation amplitude of the signal corresponding to the second-colored light. The determined modulation ratio may correspond to an estimated blood-oxygen saturation value.

Many traditional optical blood-oxygen saturation measurement devices are single-purpose devices used in controlled environments by highly trained individuals. The hardware that produces light for performing optical measurements is designed and manufactured to produce light in a narrow wavelength band, making it expensive and difficult to manufacture. Additionally, many traditional optical blood-oxygen saturation measurement devices must be used in controlled environments to meet operating requirements, including ambient temperature requirements. Operation outside of these operating requirements may result in unreliable measurements.

SUMMARY

Embodiments of the systems, devices, methods, and apparatuses described in the present disclosure are directed to sensing blood-oxygen saturation using wearable electronic devices, and in particular to compensating for variations in the wavelength of light emitted by wearable electronic device across different devices and in different operating conditions to achieve reliable blood-oxygen saturation measurements.

One embodiment may take the form of a method for performing a blood-oxygen saturation measurement using a wearable electronic device. The method may include the steps of emitting light at a first wavelength and a second wavelength using one or more light emitters of the wearable electronic device. The method may further include measuring a returned portion of the light that has interacted with a user. The method may further include sensing a temperature within an interior volume of the wearable electronic device. The method may further include determining an estimated blood-oxygen saturation value based at least partially on the returned portion of the light and the sensed temperature.

Another embodiment may take the form of a method for performing a blood-oxygen saturation measurement using a wearable electronic device. The method may include the steps of emitting light at a first wavelength and a second wavelength using one or more light emitters of the wearable electronic device. The method may further include measuring a returned portion of the light that has interacted with a user. The method may further include determining a drive current of at least one of the one or more light emitters. The method may further include determining an estimated blood-oxygen saturation value based at least partially on the returned portion of the light and the drive current.

Another embodiment may take the form of a wearable electronic device that includes an enclosure defining an interior volume, a measurement engine executing on a processing unit and position in the interior volume, and one or more light emitters positioned in the interior volume and configured to emit light at first and second wavelengths. The wearable electronic device may further include at least one light sensor positioned in the interior volume and configured to sense a returned portion of the light that has interacted with a user and output a sensing signal to the measurement engine in response to sensing the returned portion of the light. The wearable electronic device may further include a temperature sensor positioned in the interior volume and configured to sense a temperature within the interior volume and output a temperature signal to the measurement engine, the temperature signal indicating the temperature. The measurement engine may be configured to determine an estimated blood-oxygen saturation value at least partially based on the sensing signal and the temperature signal.

In addition to the example aspects and embodiments described above, further aspects and embodiments will become apparent by reference to the drawings and by study of the following description.

BRIEF DESCRIPTION OF THE DRAWINGS

The disclosure will be readily understood by the following detailed description in conjunction with the accompanying drawings, wherein like reference numerals designate like structural elements, and in which.

Figure 1:
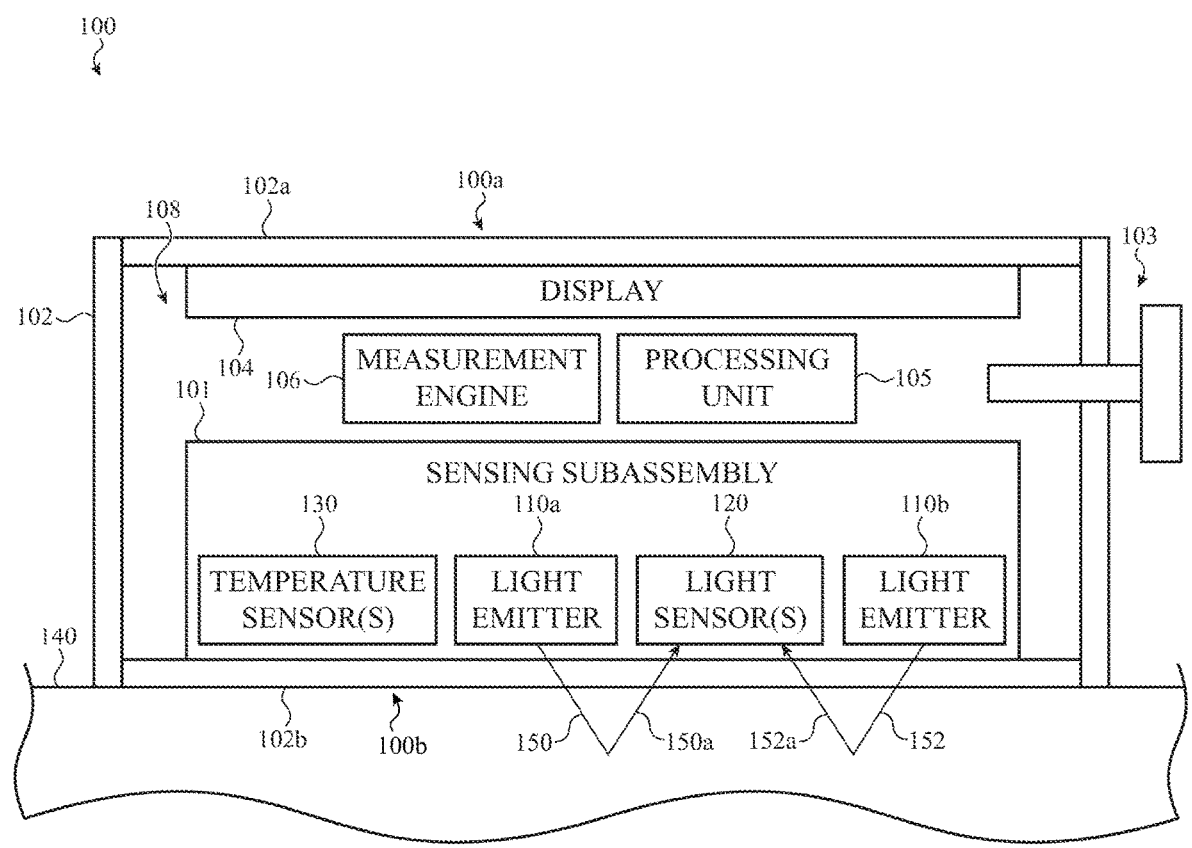
FIG. 1 is a functional block diagram of an example wearable electronic device that may be used to perform blood-oxygen saturation sensing.

The use of cross-hatching or shading in the accompanying figures is generally provided to clarify the boundaries between adjacent elements and also to facilitate legibility of the figures. Accordingly, neither the presence nor the absence of cross-hatching or shading conveys or indicates any preference or requirement for particular materials, material properties, element proportions, element dimensions, commonalities of similarly illustrated elements, or any other characteristic, attribute, or property for any element illustrated in the accompanying figures.

Additionally, it should be understood that the proportions and dimensions (either relative or absolute) of the various features and elements (and collections and groupings thereof) and the boundaries, separations, and positional relationships presented therebetween, are provided in the accompanying figures merely to facilitate an understanding of the various embodiments described herein and, accordingly, may not necessarily be presented or illustrated to scale, and are not intended to indicate any preference or requirement for an illustrated embodiment to the exclusion of embodiments described with reference thereto.

DETAILED DESCRIPTION

Reference will now be made in detail to representative embodiments illustrated in the accompanying drawings. It should be understood that the following description is not intended to limit the embodiments to one preferred embodiment. To the contrary, it is intended to cover alternatives, modifications, and equivalents as can be included within the spirit and scope of the described embodiments as defined by the appended claims.

The following disclosure relates to performing optical blood-oxygen saturation measurements using wearable electronic devices, and in particular to correcting for variations in the wavelengths of light emitted by wearable electronic devices to achieve reliable blood-oxygen saturation measurements.

A wearable electronic device may include one or more light emitters and one or more light sensors for performing optical blood-oxygen saturation measurements. One or more light emitters may emit light having a first wavelength and light having a second wavelength. One or more light sensors may detect returned light that has interacted with a user. A measurement engine of the wearable electronic device may determine an estimated blood-oxygen saturation value by analyzing changes to the light resulting from interacting with the user.

In various embodiments the actual wavelength of emitted light may vary to a significant extent, which requires compensation to avoid or reduce resulting errors in estimated blood-oxygen saturation values. The wavelength variations may be the result of inherent device characteristics of the light emitter(s) resulting from manufacturing variability or other causes. The wavelength variations of the emitted light may additionally or alternatively be the result of variations in the temperature and/or the drive current of the light emitter(s) resulting from environmental conditions, device operational conditions, or other causes. The embodiments described herein are directed to compensating for wavelength variations of emitted light to provide more reliable blood-oxygen saturation measurements.

The measurement engine of the wearable electronic device may compensate for wavelength variations in multiple ways. In some cases, determining an estimated blood-oxygen saturation value is based at least partially on temperature data that may be used to compensate for temperature-based wavelength variations of the emitted light, drive current data that may be used to compensate for drive-current-based wavelength variations of the emitted light, and/or calibration information that may be used to compensate for manufacturing variability across different light emitters. In various embodiments, the measurement engine may use temperature data, drive current data, and/or calibration information in a variety of ways to determine estimated blood-oxygen saturation values, including using lookup tables or calibration curves, applying functions, and the like.

The measurement engine of the wearable electronic device may use temperature data, drive current data, and/or calibration information to determine one or more estimated wavelength values for the light emitted by one or more light emitters. The measurement engine may use the estimated wavelength value(s) and a determined modulation ratio determine an estimated blood-oxygen saturation value. As one example, the measurement engine may use the estimated wavelength value(s) to select a calibration curve of a set of calibration curves that can be used to correlate the modulation ratio to the estimated blood-oxygen saturation value. In some cases, the measurement engine may omit or replace the intermediate step of determining the estimated wavelength(s). For example, the estimated blood-oxygen saturation value may be determined using a function or lookup table based on the modulation ratio, the temperature data, the drive current data, and/or the calibration information.

The temperature data may include one or more temperature values sensed at the wearable electronic device (e.g., a temperature within an interior volume of the wearable electronic device). Additionally or alternatively, the temperature data may include one or more estimated temperature values of one or more light emitters (e.g., an estimated junction temperature for a light emitter). An estimated temperature value for a light emitter may be determined by using a temperature estimation function (e.g., a temperature model) based on one or more sensed temperatures (e.g., a temperature sensed at a location within the wearable electronic device different from the location of a light emitter) and/or a determined drive current of the light emitter.

The wearable electronic devices described herein may include one or more temperature sensors for sensing temperature values (e.g., temperatures within an interior volume of the wearable electronic devices). In some cases, the temperature sensor(s) may be collocated with one or more light emitters. Additionally or alternatively, the temperature sensor(s) may be positioned at different locations from the light emitters.

The drive current data may include one or more measured or determined drive currents of one or more light emitters. The measurement engine of the wearable electronic devices described herein may be configured to determine a drive current of a light emitter by measuring, sensing, or otherwise determining a current flowing to or through the light emitter, by measuring, sensing, or otherwise determining a voltage drop across the light emitter, and/or any other suitable techniques for determining drive current.

The functions, lookup tables, calibration curves, and the like that are used to determine the estimated blood-oxygen saturation values and/or intermediate parameters (e.g., estimated temperatures, estimated wavelength values, and the like) may be determined based on calibration information determined during one or more calibration processes of the light emitters. For example, a calibration process may be used to determine one or more wavelengths of light emitted by one or more light emitters under known conditions, including at known temperatures and/or drive currents. In some cases, calibration information is used to construct, refine, or otherwise customize functions, lookup tables, calibration curves, and the like for a particular light emitter.

As used herein, the term "light emitter" may refer to a spatially located source of light. A light emitter may include one or more light sources, including light-emitting diodes (LEDs), laser diodes, and the like. A light emitter may emit light in response to a signal, such as a control signal from a measurement engine or a processing unit or a current applied to the light emitter. In some cases, the wavelength of light emitted by a light emitter is not controllable, and the light emitter is used to emit light at a particular wavelength. Alternatively, the wavelength of light emitted by a light emitter may be controllable As used herein, the term "wavelength" may refer to a single wavelength value or a relatively narrow range of wavelengths (e.g., a 2 nm or 5 nm range) in which the light has substantially the same optical properties, such as color.

The term "physically coupled," as used herein, may refer to two or more elements, structures, objects, components, parts or the like that are physically attached to one another. As used herein, "operably coupled" or "electrically coupled" may refer to two or more devices that operate with one another, communicate with one another, are in electrical connection with one another, and/or otherwise interact with one another in any suitable manner for operation and/or communication, including wired, wirelessly, or some combination thereof.

These and other embodiments are discussed with reference to FIGS. 1-7. However, those skilled in the art will readily appreciate that the detailed description given herein with respect to these figures is for explanatory purposes only and should not be construed as limiting.

FIG. 1 is a functional block diagram of an example wearable electronic device 100 that may be used to perform blood-oxygen saturation sensing. The wearable electronic device 100 may include a sensing assembly 101, which includes one or more light emitters 110a, 110b, one or more light sensors 120, and one or more temperature sensors 130. In some cases, the light emitters 110a, 110b form an emitter pair and are collocated within a common cavity and adapted to emit light through a common light emitting aperture. The wearable electronic device may further include a measurement engine 106 and/or a processing unit 105 for determining estimated blood-oxygen saturation values.

The wearable electronic device may further include one or more input devices (e.g., a crown 103, a button, etc.), one or more output devices (e.g., a display 104, a speaker, etc.), and a processing unit 105. The wearable electronic device 100 may include an enclosure 102 that defines an interior volume 108. The input device(s), the output device(s), the processing unit 105, the measurement engine 106, and the sensing assembly 101 may be positioned at least partially within the interior volume 108 of the enclosure 102.

The measurement engine 106 may be operably coupled to the processing unit 105 and the sensing assembly 101. In some cases, all or part of the measurement engine 106 is implemented as computer-executable code executing on the processing unit 105. In some cases, all or part of the measurement engine 106 may include or be implemented by dedicated hardware, including a dedicated processing unit. In some cases, all or part of the measurement engine 106 is included in the sensing assembly 101. Additionally or alternatively, allow part of the measurement engine 106 may be implemented on a separate device that is operably coupled to the wearable electronic device 100.

Broadly, the light emitters 110a, 110b emit light, the light sensors 120 sense light, and the temperature sensor 130 senses one or more internal temperatures of the wearable electronic device 100 during blood-oxygen saturation sensing operations. The measurement engine 106 may determine estimated blood-oxygen saturation values based on the sensed light, the sensed internal temperature(s), and/or one or more drive current(s) of the light emitters 110a, 110b. The measurement engine 106 may compensate for wavelength variation of the light emitters 110a, 110b using the sensed internal temperature(s), and/or one or more drive current(s) of the light emitters.

In an example blood-oxygen saturation sensing process, a first light emitter 110a may emit light 150 at a first wavelength (or in a first wavelength range) in response to a drive current being applied to the first light emitter, for example in response to an instruction by the measurement engine 106 and/or the processing unit 105. A second light emitter 110b may emit light 152 at a second wavelength (or in a second wavelength range) in response to a drive current being applied to the second light emitter, for example in response to an instruction by the measurement engine 106 and/or the processing unit 105.

In some cases, the light 150 emitted at the first wavelength is red and the light 152 emitted at the second wavelength is infrared, or vice versa. In some cases, the light 150 emitted at the first wavelength is red light having a peak wavelength between 625 and 700 nanometers, and the second light 152 emitted at the second wavelength is infrared light having a peak wavelength between 800 and 950 nanometers. As used herein, infrared light may refer to infrared light and/or near-infrared light. In other embodiments, the light 150, 152 may be any suitable color or wavelength as long as the wavelengths are sufficiently different from one another to determine a meaningful modulation ratio.

The light 150 and the light 152 travel toward the user 140 (e.g., through the cover 102b of the enclosure 102) and interact with the user. As described herein, light interacting with a user may include a portion of the light being absorbed by the user's tissue (e.g., skin, blood vessels, muscles, and the like), and a portion of the light being returned (e.g., reflected, scattered, etc.) from the user.

A returned portion 150a of the light 150 in the first wavelength range travels from the user to the wearable electronic device 100, where it is sensed by the light sensor 120. The light sensor 120 may output a sensing signal to the measurement engine 106 in response to detecting the returned portion 150a of the light 150. The returned portion 152a of the light 152 travels from the user to the wearable electronic device 100, where it is sensed by the light sensor 120. The light sensor 120 may output a sensing signal to the measurement engine 106 in response to detecting the returned portion 152a of the light 152.

In some cases, the same light sensor is used to sense returned portions of the light 150, 152 emitted by both light emitters 110a, 110b. Additionally or alternatively, a returned portion 150a of the light 150 and a returned portion 152a of the light 152 may be sensed by different light sensors. In some cases, multiple light sensors sense returned portions 150a, 152a of the light 150, 152.

The sensing signals may represent waveforms of the returned portions 150a, 152a. Each waveform may include a pulsatile component and a non-pulsatile component. The measurement engine 106 may determine the amplitudes of the pulsatile components and the non-pulsatile components. The measurement engine 106 may determine a modulation amplitude from each sensing signal by dividing an amplitude of the pulsatile component of the sensing signal by an amplitude of the non-pulsatile component of the sensing signal. The measurement engine 106 may determine a modulation ratio by dividing the modulation amplitude of the sensing signal corresponding to the light 150 by the modulation amplitude of the sensing signal corresponding to the light 152.

The measurement engine 106 may use the determined modulation ratio to determine an estimated blood-oxygen saturation value. In various embodiments the actual wavelength of light 150 and/or light 152 may vary to a significant extent, which requires compensation to avoid or reduce resulting errors in estimated blood-oxygen saturation values. The wavelength variations of the emitted light 150 and 152 may be the result of inherent device characteristics of the light emitters 110a, 110b resulting from manufacturing variability or other causes. The wavelength variations of the emitted light 150 and 152 may additionally or alternatively be the result of variations in the temperature of the light emitters 110a, 110b resulting from environmental conditions, device operational conditions, or other causes. The wavelength variations of the emitted light 150 and 152 may additionally or alternatively be the result of variations in the drive current applied to the light emitters 110a, 110b.

The determination of the estimated blood-oxygen saturation value from the modulation ratio may be sensitive to the actual wavelength of the light 150 and/or the light 152. For example, a particular determined modulation ratio may correspond to multiple different estimated blood-oxygen saturation values depending on the wavelength of the light 150 and/or the light 152. In some cases, the determination is more sensitive to the wavelength of the light 150 than the wavelength of the light 152, or vice versa. In some cases, the determination is only meaningfully sensitive to one of the variation in the wavelength of the light 150 or the variation in the wavelength of the light 152. For example, in embodiments in which the light 150 is red and the light 152 is infrared, the determination may be significantly more sensitive to the variation in the wavelength of the red light 150. As a result, the measurement engine 106 may only need to compensate for variations in the wavelength of the red light.

The measurement engine 106 may compensate for wavelength variations in multiple ways. In some cases, determining an estimated blood-oxygen saturation value is based at least partially on temperature data received from the temperature sensor 130 that may be used to compensate for temperature-based wavelength variations of the emitted light 150, 152. In some cases, determining an estimated blood-oxygen saturation value is based at least partially on drive current data that may be used to compensate for drive-current-based wavelength variations of the emitted light 150, 152. In some cases, determining an estimated blood-oxygen saturation value is based at least partially on calibration information that may be used to compensate for manufacturing variability across different light emitters 110a, 110b.

In various embodiments, the measurement engine 106 may determine estimated blood-oxygen saturation values that are compensated for wavelength variations in a variety of ways, including using lookup tables or calibration curves, applying functions, and the like. In some cases, the measurement engine 106 may determine an estimated blood-oxygen saturation value using a function or lookup table that takes a modulation ratio, temperature data, drive current data, and/or calibration information as inputs.

The measurement engine 106 may optionally determine one or more intermediate parameters as part of determining estimated blood-oxygen saturation values. In some cases, the measurement engine 106 may determine an estimated wavelength of the light 150 and/or the light 152 using the temperature data, the drive current data, and/or the calibration information, and then use the estimated wavelength(s) and the modulation ratio to determine the estimated blood-oxygen saturation value. Additionally or alternatively, the measurement engine 106 may determine an estimated temperature of the light emitter 110a and/or the light emitter 110b using the temperature data, the drive current data, and/or the calibration information, and then use the estimated temperature(s) and the modulation ratio to determine the estimated blood-oxygen saturation value.

The estimated blood-oxygen saturation values discussed herein may be determined as a single function or multiple functions of temperature data (e.g., a sensed temperature, an estimated temperature, or the like), drive current data (e.g., a drive current), and/or a modulation ratio. Similarly, an estimated wavelength value may be determined as a single function or multiple functions of temperature data (e.g., a sensed temperature, an estimated temperature, or the like) and/or drive current data (e.g., a drive current). The functions may be determined based on calibration information. For purposes of illustration, example functions and calibration curves for determining estimated blood-oxygen saturation values are discussed below.

As noted above, the measurement engine 106 may determine an estimated wavelength of the light 150 and/or the light 152 as part of determining an estimated blood-oxygen saturation value. The estimated wavelength(s) may be determined using a wavelength estimation function of the drive current applied to the light emitter 110a, 110b and/or an internal temperature of the wearable electronic device 100.

In one example embodiment, the wavelength estimation function may be expressed as shown in Equation 1 below, in which $\lambda_{est}$ is the estimated wavelength, $\lambda_0$ is a nominal wavelength, $T_{int}$ is an internal temperature sensed using the temperature sensor 130, and $i_e$ is the drive current of the light emitter 110a, 110b.

$$\lambda_{est} = \lambda_0 + f(T_{int}) + f(i_e) \quad \text{(Equation 1)}$$

As shown in Equation 1, the wavelength estimation function may apply wavelength offsets to a nominal wavelength to determine the estimated wavelength. The nominal wavelength may be determined during a calibration process, and may correspond to a wavelength of the light at a known temperature and/or drive current. The wavelength offsets may include a first wavelength offset that is a function of the internal temperature (e.g., $f(T_{int})$) and/or a second wavelength offset that is a function of the drive current of the light emitter 110a, 110b (e.g., f(i_e)).

In one example embodiment, a temperature-based wavelength offset function (e.g., f($T_{int}$)) may be expressed as shown in Equation 2 below, in which f($T_{int}$) is the wavelength offset, $K_{temp}$ is a temperature coefficient determined during calibration, $T_{int}$ is the internal temperature, To is a nominal temperature determined during calibration.

$$f(T_{int})=K_{temp}(T_{int}-T_0) \quad \text{(Equation 2)}$$

As shown in Equation 2, the wavelength offset that is a function of the internal temperature of the wearable electronic device 100 determines a temperature difference between the internal temperature and a nominal temperature and multiplies that temperature difference by a temperature coefficient. The nominal temperature may be a temperature at which no temperature-based wavelength correction is necessary. As shown in Equation 2, if the internal temperature equals the nominal temperature, the wavelength offset equals zero.

In some cases, the wavelength estimation function, including the wavelength offset functions, may be determined during a calibration process and/or based on calibration information. The calibration process may include emitting light using the light emitter 110a, 110b in test conditions (e.g., at one or more test temperatures and/or with one or more test drive currents) and determining the impacts of different temperatures and/or drive currents on the wavelength of the light emitted by the light emitter 110a, 110b. The calibration process used to determine the functions above may be performed during manufacturing or after manufacturing. The calibration process may be specific to a particular wearable electronic device 100. That is, a separate calibration process may be performed for each wearable electronic device 100 that is manufactured.

In some cases, a determined modulation ratio may correspond to an estimated blood-oxygen saturation value in a calibration curve stored by (or otherwise accessible to) the wearable electronic device 100. The wearable electronic device 100 may store (or otherwise be able to access) a set of calibration curves that correlate modulation ratios with estimated blood-oxygen saturation values for different wavelengths of the light 150 and/or the light 152. The calibration curves in a set of calibration curves may be determined during a calibration process in which wavelengths and true values for blood-oxygen saturation are known. Example calibration curves are discussed in more detail with respect to FIG. 5. In some cases, the measurement engine 106 may determine an estimated wavelength of the light 150 and/or the light 152, and may select which calibration curve of the set of calibration curves to use based on the estimated wavelength(s).

The example functions and calibration curves discussed above are for illustrative purposes and are not meant to be limiting. In various embodiments, estimated blood-oxygen saturation values or other intermediate parameters may be determined using any suitable functions, lookup tables, and the like.

In various embodiments, the light emitters 110a, 110b may form an emitter pair. In some cases, the sensing assembly 101 may include multiple emitter pairs. The light emitters of an emitter pair may be collocated (e.g., placed close to one another, placed in the same cavity, or the like) so that when the light emitted by each have similar signal paths and, accordingly, can be compared more effectively. For example, the light detected from collocated emitter pairs may be less likely to have variations due to having significantly different signal paths through the user and elsewhere. In various embodiments, the sensing assembly 101 may include one or more light emitters that are not part of emitter pairs and/or are not collocated with other emitters.

As noted above, in various embodiments, a first light emitter 110a of an emitter pair may emit light at a first wavelength and a second light emitter 110b of an emitter pair may emit light at a second wavelength different from the first wavelength, and sensed portions of the light emitted by each light emitter may be compared to determine a modulation ratio and/or a blood-oxygen saturation value. In some cases, a single light sensor 120 detects returned portions of the light from both light emitters 110a, 110b in an emitter pair. The light sensor 120 may be capable of outputting multiple signals, each corresponding to light sensed by a different light emitter. In some cases, the measurement engine 106 uses a multiplexing technique in which emission and/or sensing of the light from each light emitter occurs at different times. In some cases, the measurement engine 106 may sense light from multiple emitters at the same time and use signal processing techniques to separate the signals or otherwise extract relevant information. In some cases, the sensing assembly 101 may include one or more physical components that allow the light sensor(s) 120 to sense light from multiple emitters, including filters and the like.

An emitter pair and a light sensor may form a sensing module. In some cases, the light from a light emitter 110a, 110b (or an emitter pair) may be detected by two or more light sensors 120. Similarly, a light sensor 120 may detect light from two or more emitter pairs. Each combination of an emitter pair and a light sensor forms a different sensing module. For example, a sensing assembly 101 with four emitter pairs and four light sensors includes 16 sensing modules. The sensing assembly 101 and/or the measurement engine 106 may obtaining separate sensing signals for each light emitter of the multiple emitter pairs using multiplexing, signal processing, and/or filtering techniques as described above.

In some cases, multiple sensing modules may be used to determine an estimated blood-oxygen saturation value. The signals corresponding to each sensing module may be combined in various ways to determine an estimated blood-oxygen saturation value. In some cases, a modular-estimated oxygen saturation value may be determined for each sensing module, and the measurement engine 106 may compute a mathematical average (e.g., a mean, a time-weighted average, or the like) of the modular values to determine an overall estimated blood-oxygen saturation value. Additionally or alternatively, the measurement engine 106 may determine a mathematical average of one or more intermediate parameters (e.g., a modulation ratio) determine using the signals from multiple sensing modules.

The measurement engine 106 may compensate for light-emitter wavelength variations in a variety of ways when multiple sensing modules are used to determine an overall estimated blood-oxygen saturation value. In some cases, the measurement engine 106 may apply separate compensation techniques for each light emitter and each sensing module. In some cases, the measurement engine 106 may perform global compensation techniques that correct for wavelength variations across multiple light emitters and/or sensing modules.

In some cases, the sensing assembly 101 may include one or more light emitters for performing additional biological measurements including heart rate measurements and the like. The light emitters may be configured to emit red light, infrared light, green light, white light, and/or other colors. In some cases, biological parameters may be determined using photoplethysmography (PPG). A light emitter may emit light (e.g., green light) that interacts with a user. One or more light sensors 120 may detect a portion of the emitted light that has interacted with the user and the measurement engine 106 estimate a heart rate of the user using the detected portion of the light.

As noted above, the light emitters 110a, 110b, the light sensor 120, and the temperature sensor 130 may be components of a sensing assembly 101 of the wearable electronic device 100. The sensing assembly 101 may include a sensing assembly housing that is positioned beneath the cover 102b. The sensing assembly housing may at least partially define one or more cavities in which the light emitters 110a, 110b, the light sensor 120, and the temperature sensor 130 are positioned. In some cases, one or more light emitters 110a, 110b and the temperature sensor 130 are positioned in a first cavity and the light sensor 120 is positioned in a second cavity separated from the first cavity by a wall. In some cases, the temperature sensor 130 is in a different cavity from the light emitters 110a, 110b and/or the light sensor(s) 120. Various example arrangements of the components of the sensing assembly 101 are discussed in more detail below with respect to FIGS. 3A-4C.

In some cases, each light emitter 110a, 110b includes one or more light sources (e.g., LEDs, laser diodes, and the like). Each light emitter 110a, 110b may be configured to emit light at one or more wavelengths of a wavelength range in response to a drive current being applied to the light emitter. As shown in FIG. 1, the light emitters 110a, 110b may be separate components. Alternatively, the light emitters 110a, 110b may be integrated into a single component that emits multiple colors of light (e.g., red light and infrared light).

As noted above, a wavelength of light emitted by a light emitter 110a, 110b may vary based on the drive current applied to the light emitter, an internal temperature of the wearable electronic device 100, and/or characteristics of the light emitter itself. The wavelength of the light emitted by a light emitter 110a, 110b may vary by 10 nm, 15, nm, or more. The embodiments described herein may allow the wavelengths of the light emitted by the light emitters 110a, 110b to be estimated within 5 nm, 2 nm, or less.

The light sensor 120 may be any suitable type of light sensor, including photoresistors, photodiodes, phototransistors, image sensors, and the like. As noted above, the light sensor 120 may output a sensing signal in response to detecting light.

The temperature sensor 130 may be any suitable type of temperature sensor, including thermistors, resistance temperature detectors (RTD), thermocouples, semiconductor-based sensors, and the like. In some cases, the temperature sensor 130 is a thermistor, such as a negative temperature coefficient (NTC) thermistor. In some cases, the temperature sensor 130 may be collocated with one or more light emitters 110a, 110b and/or the light sensors 120. Additionally or alternatively, the temperature sensor 130 may be located separately from one or more light emitters 110a, 110b and/or light sensors 120. In various embodiments, the sensing assembly 101 may include multiple temperature sensors 130. In some cases, a temperature sensor 130 is collocated with each light emitter of the sensing assembly 101. For example, there may be a temperature sensor 130 in each cavity within which a light emitter is located. The temperatures sensed by each temperature sensor 130 may be used to correct for wavelength variations of its respective collocated light emitter.

The drive current applied to the light emitter(s) 110a, 110b may be measured or sensed by the measurement engine 106. For example, the measurement engine 106 may include or be operably coupled to an ammeter that is connected in series with the light emitter 110a, 110b. In some cases, the measurement engine 106 may determine the drive current applied to the light emitter(s) 110a, 110b by determining a voltage drop across the light emitter(s) and dividing the voltage by a known resistance of the light emitter(s). In some cases, the measurement engine 106 may control the drive current applied to the light emitters 110a, 110b. The drive current applied to the light emitter(s) 110a, 110b may be a calibrated value such that the measurement engine 106 can apply a known drive current to the light emitter(s).

The display 104 may be positioned at least partially within the enclosure 102. The display 104 provides a graphical output, for example associated with an operating system, user interface, and/or applications of the electronic device 100. In one embodiment, the display 104 includes one or more sensors and is configured as a touch-sensitive (e.g., single-touch, multi-touch) and/or force-sensitive display to receive inputs from a user. The display 104 is operably coupled to the processing unit 105 of the electronic device 100. In some cases, the graphical output of the display 104 is visible along at least a portion of an external surface of the electronic device 100.

In various embodiments, a graphical output of the display 104 is responsive to inputs provided at the display and one or more additional input devices. For example, the processing unit 105 may be configured to modify the graphical output of the display 104 in response to receiving rotational inputs, receiving translational inputs, or receiving touch inputs. The graphical output of the display 104 may be responsive to biological parameters determined using the sensing assembly 101, including blood-oxygen saturation values and/or heart rate.

The display 104 can be implemented with any suitable technology, including, but not limited to liquid crystal display (LCD) technology, light emitting diode (LED) technology, organic light-emitting display (OLED) technology, organic electroluminescence (OEL) technology, or another type of display technology.

The enclosure 102 may include a cover 102a that is positioned over the display 104. The cover 102a may define a front exterior surface 100a of the wearable electronic device 100. A graphical output of the display 104 may be viewable through the cover 102a. The enclosure 102 may additionally or alternatively include a cover 102b that defines a rear exterior surface 100b of the wearable electronic device 100 opposite the front exterior surface 100a.

The sensing assembly 101 may be positioned beneath the cover 102b. In some cases, the light emitters 110a, 110b emit light through the cover 102b, and the light sensor(s) 120 sense light through the cover 102b. The cover 102b may include one or more masks that define areas having different opacity. For instance, in some cases, the mask may define one or more areas that are at least partially translucent over cavities that include light emitters 110a, 110b and/or light sensors 120, and one or more areas that are opaque over other areas. This may allow light to be emitted and sensed through the cover 102b while hiding internal components of the wearable electronic device.

The wearable electronic device 100 may include additional and/or alternative components that are not shown in FIG. 1 for simplicity. For example, the wearable electronic device 100 may include input devices, output devices, memory, a power source, and/or electrical connectors that operably couple the components of the wearable electronic device. Example components of the wearable electronic device 100 are discussed in more detail below with respect to FIG. 7.

Figure 2A:
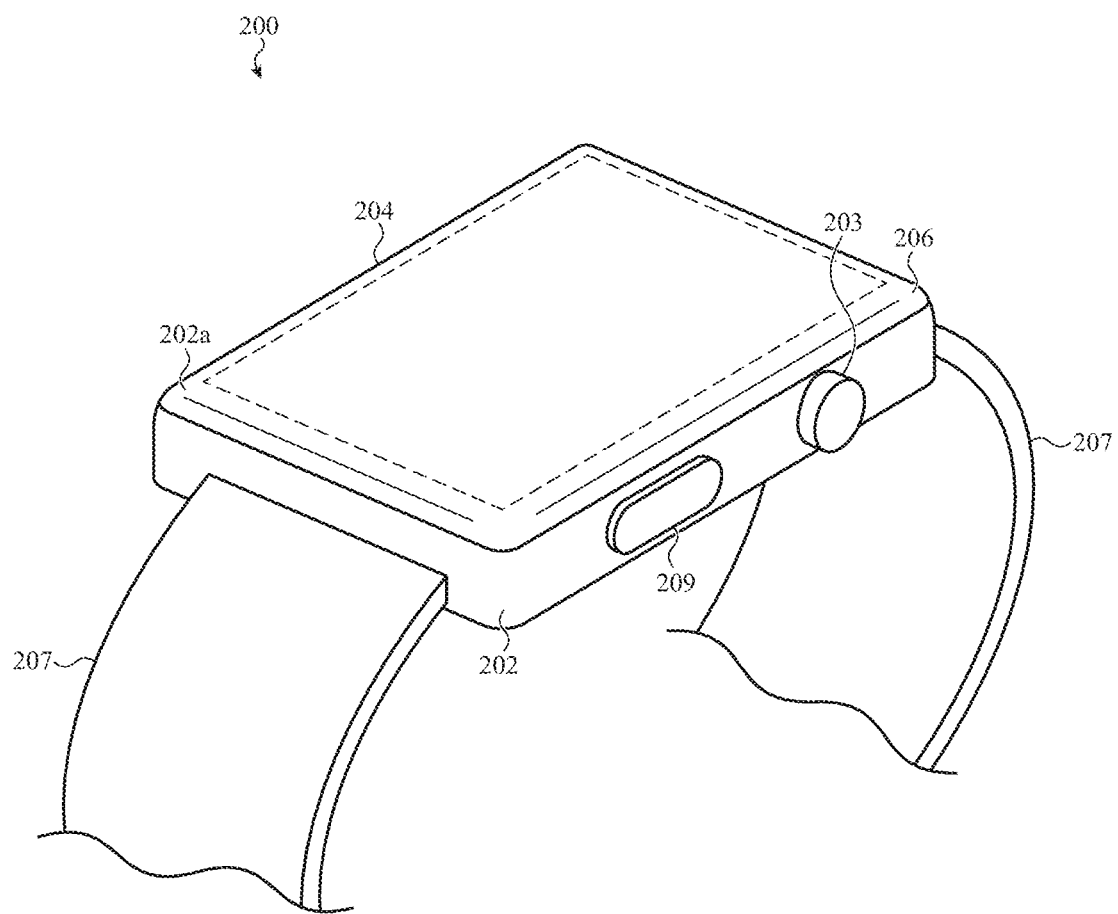
FIG. 2A illustrates an example watch that may incorporate a sensing assembly as described herein.

FIG. 2A illustrates an example watch 200 (e.g., an electronic watch or smart watch) that may incorporate a sensing assembly as described herein. The watch 200 may include a watch body 206 and a watch band 207. Other devices that may incorporate a crown assembly include other wearable electronic devices, other timekeeping devices, other health monitoring or fitness devices, other portable computing devices, mobile phones (including smart phones), tablet computing devices, digital media players, or the like. The watch 200 may have similar components, structure, and/or functionality as the wearable electronic device 100 described with respect to FIG. 1. The watch 200 may provide time and timing functions, receive messages and alerts, and may track activity of a user. In some cases, the watch may monitor biological conditions or characteristics of a user.

The watch body 206 may include an enclosure 202. The enclosure 202 may include a front side enclosure member that faces away from a user's skin when the watch 200 is worn by a user, and a back-side enclosure member that faces toward the user's skin. Alternatively, the enclosure 202 may include a singular enclosure member, or more than two enclosure members. The one or more enclosure members may be metallic, plastic, ceramic, glass, or other types of enclosure members (or combinations of such materials).

The enclosure 202 may include a cover 202*a* mounted to a front side of the watch body 206 (i.e., facing away from a user's skin) and may protect a display 204 mounted within the enclosure 102. The display 204 may produce graphical output that may be viewable by a user through the cover 202*a*. In some cases, the cover 202*a* may be part of a display stack, which may include a touch sensing or force sensing capability. The display may be configured to depict a graphical output of the watch 200, and a user may interact with the graphical output (e.g., using a finger, stylus, or other pointer). As one example, the user may select (or otherwise interact with) a graphic, icon, or the like presented on the display by touching or pressing (e.g., providing touch input) on the cover 202*a* at the location of the graphic. As used herein, the term "cover" may be used to refer to any transparent, semi-transparent, or translucent surface made out of glass, a crystalline material (such as sapphire or zirconia), plastic, or the like. Thus, it should be appreciated that the term "cover," as used herein, encompasses amorphous solids as well as crystalline solids. The cover 202*a* may form a part of the enclosure 202. In some examples, the cover 202*a* may be a sapphire cover. The cover 202*a* may also be formed of glass, plastic, or other materials.

The watch body 206 may include at least one input device or selection device, such as a button, crown, scroll wheel, knob, dial, or the like, which input device may be operated by a user of the watch 200.

The watch 200 may include one or more input devices (e.g., a crown 203, a button 209, a scroll wheel, a knob, a dial, or the like). The input devices may be used to provide inputs to the watch 200. The crown 203 and/or button 209 may be positioned along a portion of the enclosure 202, for example along a sidewall of the enclosure as shown in FIG. 2. In some cases, the enclosure 202 defines an opening through which a portion of the crown 203 and/or the button 209 extends.

The crown 203 may be user-rotatable, and may be manipulated (e.g., rotated, pressed) by a user. The crown 203 and/or button 209 may be mechanically, electrically, magnetically, and/or optically coupled to components within the enclosure 202, as one example. A user's manipulation of the crown 203 and/or button 209 may be used, in turn, to manipulate or select various elements displayed on the display, to adjust a volume of a speaker, to turn the watch 200 on or off, and so on.

In some embodiments, the button 209, the crown 203, scroll wheel, knob, dial, or the like may be touch sensitive, conductive, and/or have a conductive surface, and a signal route may be provided between the conductive portion and a circuit within the watch body 206, such as a processing unit.

The enclosure 202 may include structures for attaching the watch band 207 to the watch body 206. In some cases, the structures may include elongate recesses or openings through which ends of the watch band 207 may be inserted and attached to the watch body 206. In other cases (not shown), the structures may include indents (e.g., dimples or depressions) in the enclosure 202, which indents may receive ends of spring pins that are attached to or threaded through ends of a watch band to attach the watch band to the watch body. The watch band 207 may be used to secure the watch 200 to a user, another device, a retaining mechanism, and so on.

In some examples, the watch 200 may lack any or all of the cover 202*a*, the display 204, the button 209, or the crown 203. For example, the watch 200 may include an audio input or output interface, a touch input interface, a force input or haptic output interface, or other input or output interface that does not require the display 204, the button 209, or the crown 203. The watch 200 may also include the aforementioned input or output interfaces in addition to the display 204, the button 209, or the crown 203. When the watch 200 lacks the display, the front side of the watch 200 may be covered by the cover 202*a*, or by a metallic or other type of enclosure member.

Figure 2B:
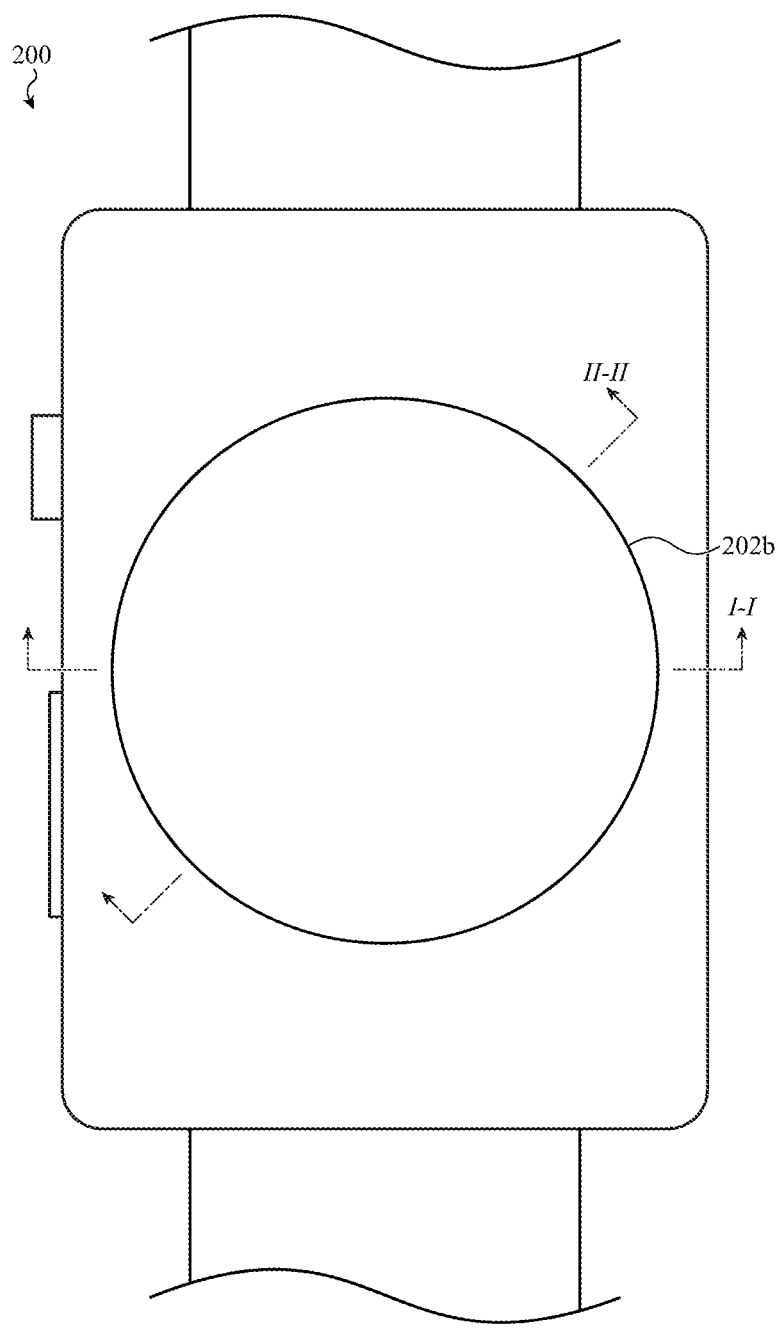
FIG. 2B illustrates a rear view of the example watch of FIG. 2A.

FIG. 2B illustrates a rear view of the example watch 200 of FIG. 2A. As shown in FIG. 2B, the watch 200 may include a rear cover 202*b* that defines a rear exterior surface of the watch. In some cases, the cover 202*b* may have one or more electrodes thereon. The one or more electrodes on the cover 202*b* may be used to determine a biological parameter, such as a heart rate, an electrocardiogram, or the like. In some cases, the electrodes are used in combination with one or more additional electrodes, such as a surface of a crown assembly or other input device.

Figure 3A:
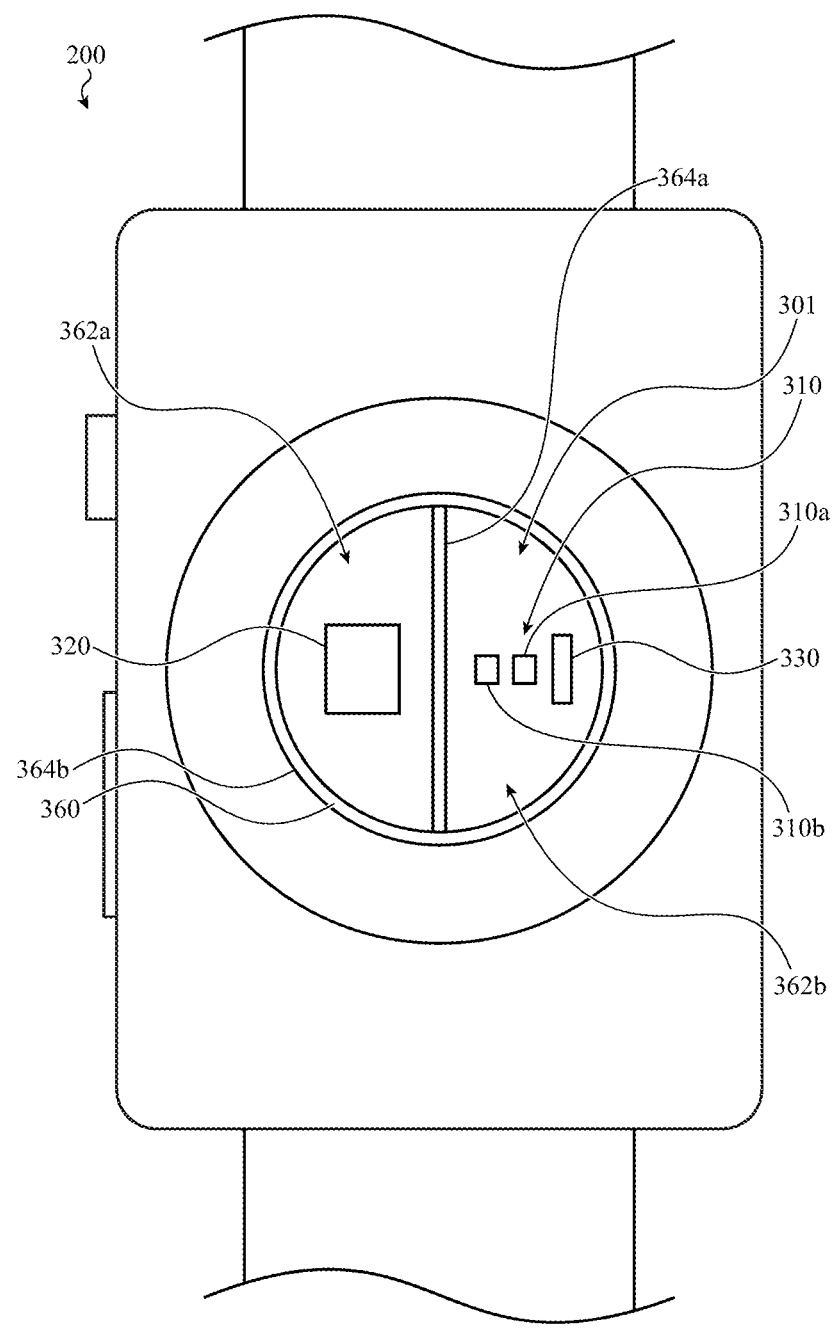
FIG. 3A illustrates a rear view of a first embodiment of the example watch of FIG. 2A showing a sensing assembly positioned beneath a rear cover.

FIG. 3A illustrates a rear view of a first embodiment of the example watch 200 with the rear cover 202*b* removed to show components of a sensing assembly 301 positioned beneath the rear cover. The sensing assembly 301 includes an emitter pair 310 that includes a first light emitter 310*a* and a second light emitter 310*b*, a temperature sensor 330, and a light sensor 320. The first light emitter 310*a* may emit light at a first wavelength (e.g., red light) and the second light emitter 310*b* may emit light at a second wavelength (e.g., infrared light) as part of a blood-oxygen saturation sensing process. The light sensor 320 may detect returned portions of the emitted light and output corresponding sensing signals to a measurement engine of the watch 200 for use in determining an estimated blood-oxygen saturation value. The temperature sensor 330 may sense an internal temperature of the watch 200 that may be used to compensate for variations in the wavelength of the light emitted by the first light emitter 310*a* and/or the second light emitter 310*b*.

The sensing assembly 301 may include a sensing assembly housing 360 that houses some or all of the components of the sensing assembly. The sensing assembly housing 360 may be attached to the cover 202*b* as described below with respect to FIG. 3B. The sensing assembly housing 360 may define one or more cavities (e.g., cavities 362*a*, 362*b*) that are defined by one or more walls 364*a*, 364*b* (e.g., light blocking walls) of the sensing assembly housing. One or more of the walls (e.g., wall 364*a*) may separate the cavities 362*a*, 362*b*. One or more of the walls (e.g., wall 364*b*) may at least partially surround the light emitters 310*a*, 310*b*, the temperature sensor 330, and/or the light sensor 320.

Each of light emitters 310*a*, 310*b*, the light sensor 320, and the temperature sensor 330 may be positioned in a cavity 362*a*, 362*b*. As shown in FIG. 3A, the light emitter 310*a*, the light emitter 310*b*, and/or the temperature sensor 330 may be collocated in a cavity 362*b*. This may allow the light emitters 310*a*, 310*b* to have similar signal paths to the light sensor 320 and/or it may result in more accurate sensing of the temperatures (e.g., junction temperatures) of the light emitters. In various embodiments, the light sensor 320 may be positioned in a different cavity from the light emitters 310*a*, 310*b* to prevent or reduce the amount of light that has not interacted with a user from being detected by the light sensor. In some cases, the temperature sensor 330 may be positioned in a different cavity from the light emitters 310*a*, 310*b*.

Figure 3B:
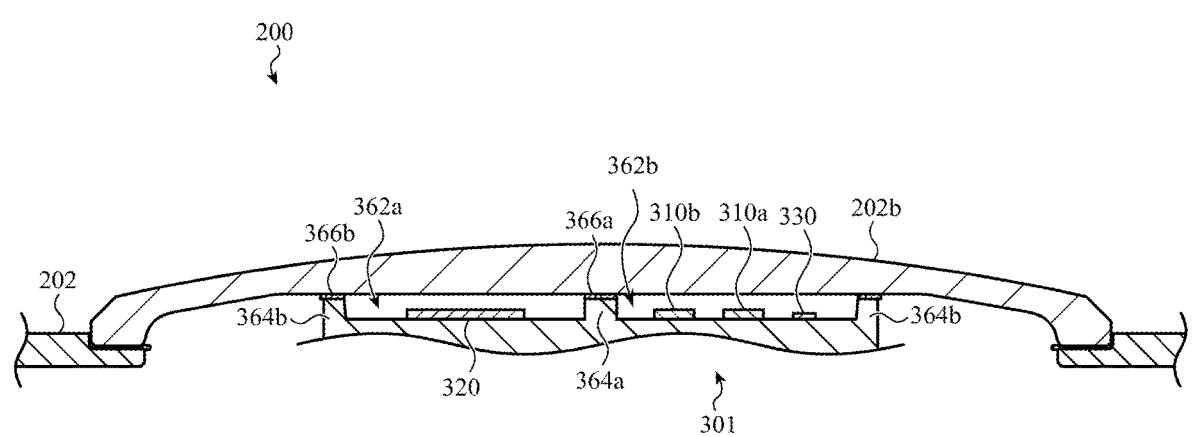
FIG. 3B illustrates a partial cross-section view of the first embodiment of the example watch of FIG. 2A, taken through section line I-I of FIG. 2B.

FIG. 3B illustrates a partial cross-section view of the first embodiment of the example watch 200, taken through section line I-I of FIG. 2B. FIG. 3B illustrates the sensing assembly 301 positioned in an interior volume of the enclosure 202 and beneath the cover 202*b*. The cover 202*b* may be configured to be positioned against a user's skin (e.g., the user's wrist) during use of the watch 200. The light emitters 310*a*, 310*b* may emit light through the cover 202*b*, and the light sensor 320 may sense light through the cover 202*b*. The sensing assembly 301 may be attached to an interior surface of the cover 202*b*. For example, the walls 364*a*, 364*b* may be attached to an interior surface of the cover 202*b* using adhesive 366*a*, 366*b* or any other suitable mechanism for joining the sensing assembly housing 360 to the cover 202*b*.

Figure 4A:
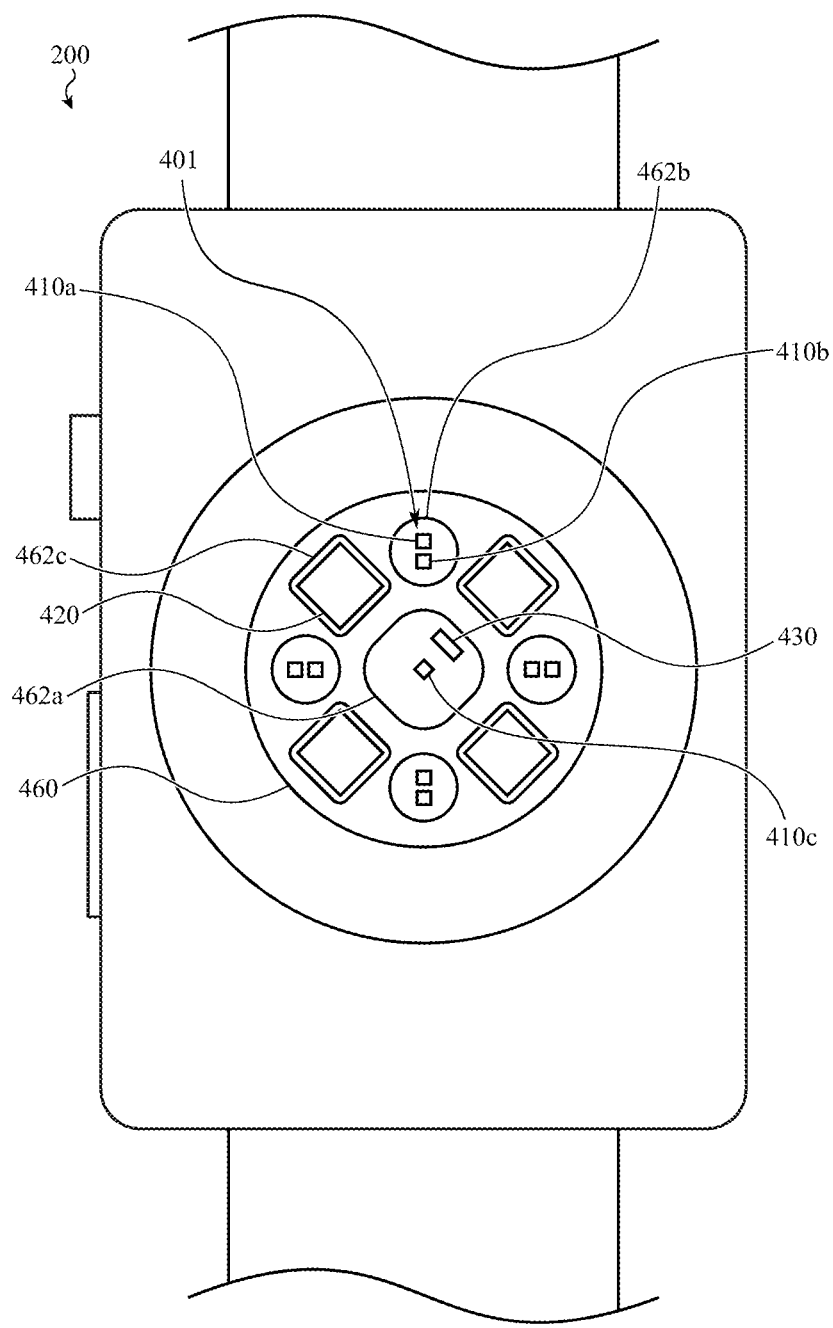
FIG. 4A illustrates a rear view of a second embodiment of the example watch of FIG. 2A showing a sensing assembly positioned beneath a rear cover.

As noted above, the sensing assemblies described herein may include multiple emitter pairs. FIG. 4A illustrates a rear view of a second embodiment of the example watch 200 with the rear cover 202*b* removed to show components of a sensing assembly 401 positioned beneath the rear cover. The sensing assembly 401 includes four emitter pairs 410 that each include a first light emitter 410*a* and a second light emitter 410*b*. The sensing assembly 401 further includes four light sensors 420 and a temperature sensor 430. The first light emitter 410*a* of one or more emitter pairs 410 may emit light at a first wavelength (e.g., red light) and the second light emitter 410*b* of one or more emitter pairs 410 may emit light at a second wavelength (e.g., infrared light) as part of a blood-oxygen saturation sensing process. The light sensor 420 may detect returned portions of the emitted light and output corresponding sensing signals to a measurement engine of the watch 200 for use in determining an estimated blood-oxygen saturation value. The temperature sensor 430 may sense an internal temperature of the watch 200 that may be used to estimate a temperature of one or more light emitters 410*a*, 410*b* to compensate for variations in the wavelength of the light emitted by the light emitters 410*a*, 410*b*.

The sensing assembly 401 may include a sensing assembly housing 460 that houses some or all of the components of the sensing assembly. The sensing assembly housing 460 may define one or more cavities (e.g., cavities 462*a*-*c*) that are defined by one or more walls (e.g., light blocking walls) of the sensing assembly housing that separate the cavities and/or surround one or more cavities.

As shown in FIG. 4A, the temperature sensor 430 may be positioned in a cavity 462*a* in a central region of the sensing assembly 401. Each emitter pair 410 may be positioned in its own cavity 462*b*, and each light sensor 420 may be positioned in its own cavity 462*c*. In various embodiments, one or more of the cavities 462*a*-*c* may include additional components, including temperature sensors, light emitters, and the like. In some cases, for example, one or more of the cavities 462*a* include a temperature sensor for more precisely estimating a temperature of the light emitters 410*a*, 410*b* in each cavity. As shown in FIG. 4A, the emitter pairs 410 and the light sensors 420 and their respective cavities 462*b*, 462*c* may be positioned in a peripheral region of the sensing assembly 401 that surrounds the central region. As such, the light sensors 420 and their respective cavities 462*b*, 462*c* may at least partially surround the cavity 462*a* and the temperature sensor 430.

As shown in FIG. 4A, the sensing assembly 401 may further include a light emitter 410*c*. The light sensor 410*c* may be used to perform additional biological measurements including heart rate measurements and the like. In some cases, biological parameters may be determined using photoplethysmography (PPG). The light emitter 410*c* may be configured to emit red light, infrared light, green light, white light, and/or other colored light that interacts with a user. One or more light sensors 420 may detect a portion of the emitted light that has interacted with the user and the measurement engine of the watch 200 may estimate a heart rate of the user using the detected portion of the light. As shown in FIG. 4A, the light sensor 410*c* may be positioned beneath a central region of the cover 202*b*. The light sensor 410*c* may be positioned in a cavity with the temperature sensor 430 and/or other components of the sensing assembly 401.

Figure 4B:
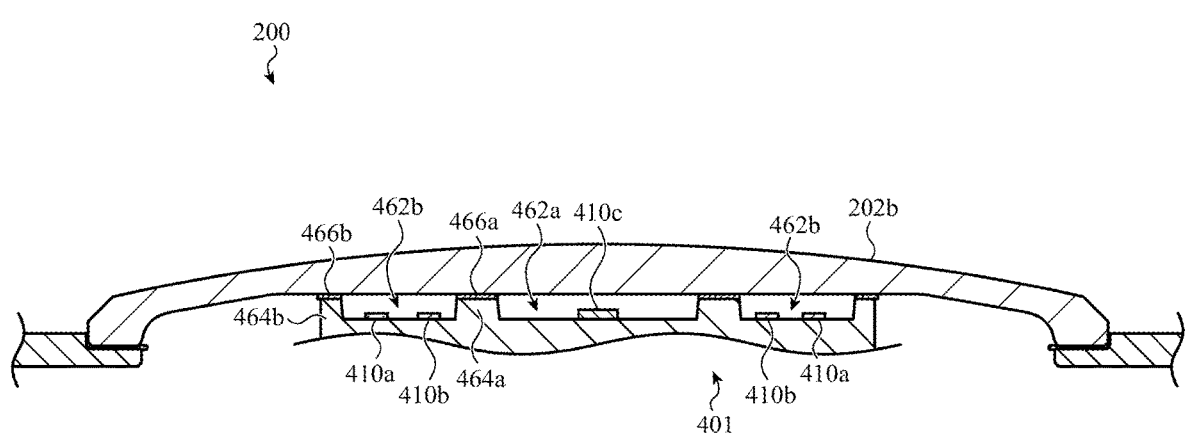
FIGS. 4B and 4C illustrate partial cross-section views of the second embodiment of the example watch of FIG. 2A, taken through section lines I-I and II-II of FIG. 2B, respectively.
Figure 4C:
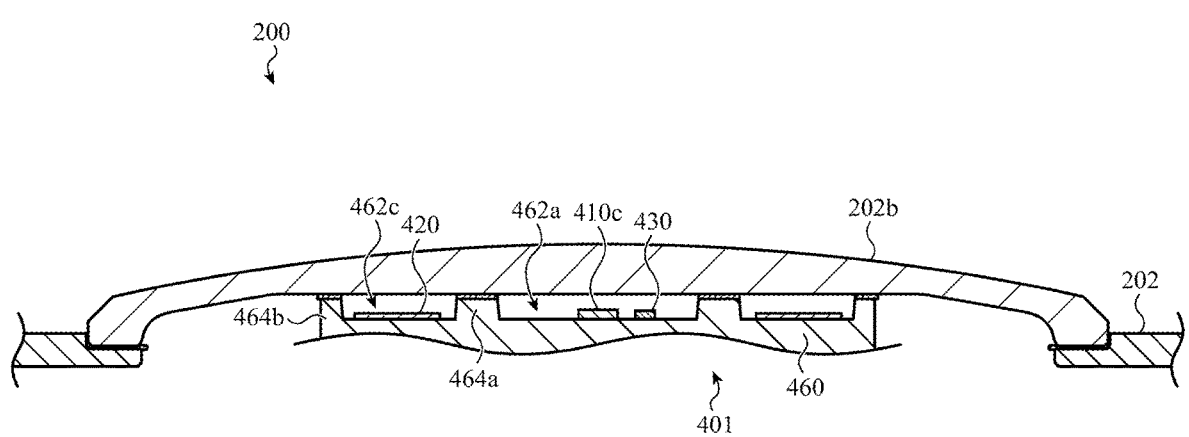

FIGS. 4B and 4C illustrate partial cross-section views of the second embodiment of the example watch 200, taken through section lines I-I and II-II of FIG. 2B, respectively. As noted above, the cover 202*b* may be configured to be positioned against a user's skin (e.g., the user's wrist) during use of the watch 200. The light emitters 410*a*, 410*b* may emit light through the cover 202*b*, and the light sensor 420 may sense light through the cover 202*b*. The sensing assembly 401 may be attached to an interior surface of the cover 202*b*. For example, the walls 464*a*, 464*b* may be attached to an interior surface of the cover 202*b* using adhesive 466*a*, 466*b* or any other suitable mechanism for joining the sensing assembly housing 460 to the cover 202*b*.

Figure 5:
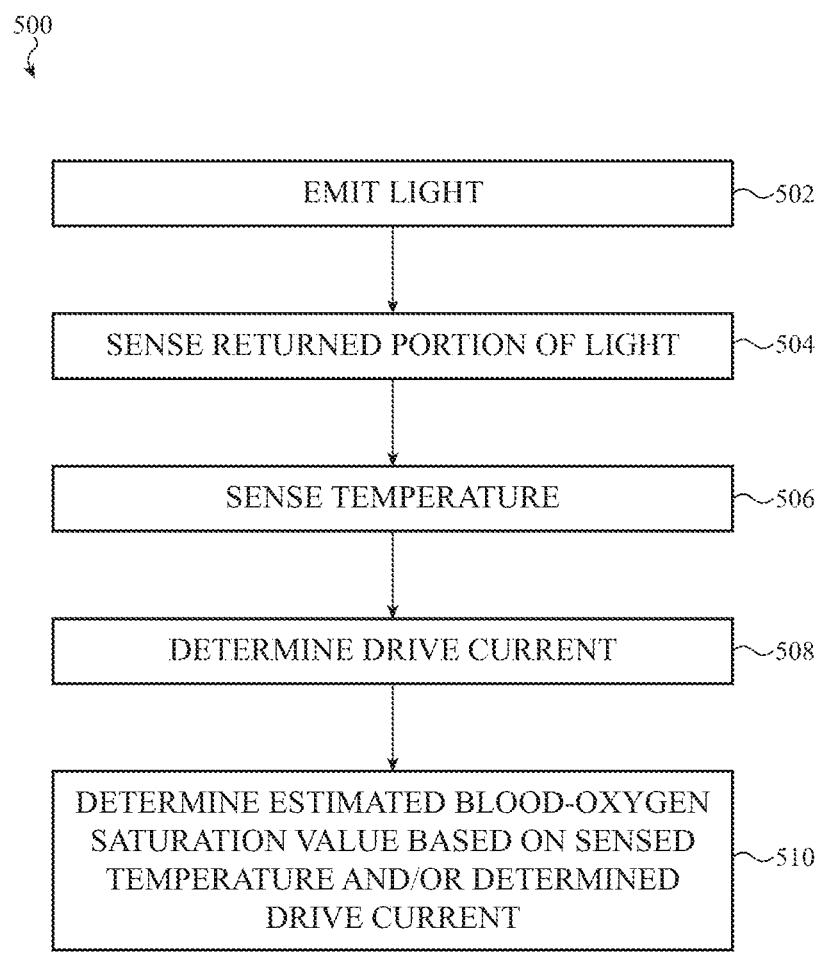
FIG. 5 is a flowchart depicting example operations of a method for determining an estimated blood-oxygen saturation value.

FIG. 5 is a flowchart depicting example operations of a method 500 for determining an estimated blood-oxygen saturation value. The method 500 can be performed in whole or in part by one or more hardware resources of a wearable electronic device (e.g., wearable electronic devices 100, 200).

At operation 502, one or more light emitters of the wearable electronic device emit light at a first wavelength and light at a second wavelength. The light emitter(s) may emit the light in response to an instruction by a measurement engine that causes a drive current to be applied to each light emitter. The light at the first wavelength may be red light having a peak wavelength between 625 and 700 nm. The light at the second wavelength may be infrared light having a peak wavelength between 800 and 950 nm. The light may travel toward a user (e.g., through a cover of an enclosure) and interact with the user. As described herein, light interacting with a user may include a portion of the light being absorbed by the user's tissue (e.g., skin, blood vessels, muscles, and the like), and a portion of the light being returned from the user.

At operation 504, one or more light sensors of the wearable electronic device sense the light that is returned from the user. The light sensor(s) may output sensing signals in response to sensing the returned portions of the light. The sensing signals may represent a waveform of the returned portions of light. In some cases, a first sensing signal represents a waveform of the returned portion of the light at the first wavelength and the second sensing signal represents a waveform of the returned portion of the light at the second wavelength.

At operation 506, a temperature sensor of the wearable electronic device senses a temperature. The temperature may be an internal temperature of the wearable electronic device (e.g., a temperature within the interior volume of the wearable electronic device). In some cases, the temperature is a temperature of a cavity of the wearable electronic device containing the temperature sensor and/or one or more light emitters. The temperature sensor may output a temperature signal to the measurement engine that indicates the sensed temperature.

At operation 508, the measurement engine of the wearable electronic device determines a drive current of one or more light emitters. The drive currents may be expressed as single values or multiple values (e.g., waveforms).

The measurement engine of the wearable electronic device may determine one or more intermediate parameters, such as one or more estimated temperatures (e.g., junction temperatures) of one or more light emitters of the wearable device and/or one or more estimated wavelengths of one or more light emitters of the wearable device. In some cases, the measurement engine of the wearable electronic device may determine an estimated temperature of one or more light emitters using the temperature signal, the drive current, and/or calibration information regarding the light emitters.

At operation 510, the measurement engine determines an estimated blood-oxygen saturation value based on the detected light, the temperature signal(s), the drive current(s), and/or calibration information about one or more light emitters.

In some cases, determining an estimated blood-oxygen saturation value is based at least partially on temperature data received from the temperature sensor that may be used to compensate for temperature-based wavelength variations of the emitted light. In some cases, determining an estimated blood-oxygen saturation value is based at least partially on calibration information that may be used to compensate for manufacturing variability across different light emitters. In various embodiments, the measurement engine may determine estimated blood-oxygen saturation values that are compensated for wavelength variations in a variety of ways, including using lookup tables or calibration curves, applying functions, and the like. In some cases, the measurement engine may determine an estimated blood-oxygen saturation value using a function or lookup table that takes a modulation ratio, temperature data, and/or calibration information as inputs.

The measurement engine may optionally determine one or more intermediate parameters as part of determining estimated blood-oxygen saturation values. In some cases, the measurement engine may determine an estimated wavelength of the light and/or the light using the temperature data and/or the calibration information, and then use the estimated wavelength(s) and the modulation ratio to determine the estimated blood-oxygen saturation value. Additionally or alternatively, the measurement engine may determine an estimated temperature one or more light emitters using the temperature data and/or the calibration information, and then use the estimated temperature(s) and the modulation ratio to determine the estimated blood-oxygen saturation value.

As noted above, the measurement engine of the wearable electronic device may use temperature data and/or calibration information to determine one or more estimated wavelength values for the light emitted by one or more light emitters. The measurement engine may use the estimated wavelength value(s) and a determined modulation ratio determine an estimated blood-oxygen saturation value. As one example, the measurement engine may use the estimated wavelength value(s) to select a calibration curve of a set of calibration curves that can be used to correlate the modulation ratio to the estimated blood-oxygen saturation value. In some cases, the measurement engine may omit or replace the intermediate step of determining the estimated wavelength(s). For example, the estimated blood-oxygen saturation value may be determined using a function or lookup table based on the modulation ratio, the temperature data, and/or the calibration information. In some cases, the measurement engine may determine one or more estimated temperatures of light emitters of the wearable electronic device as part of determining estimated wavelengths of emitted light and/or estimated blood-oxygen saturation values.

The wearable electronic device may maintain in memory or otherwise have access to a set of calibration curves, functions, and/or lookup tables for determining estimated blood-oxygen saturation values using temperature data, calibration information, estimated temperatures, modulation ratios, different wavelengths, and the like. In some cases, the wearable electronic device may maintain in memory or otherwise have access to a set of calibration curves that correlate modulation ratios with estimated blood-oxygen saturation values for different wavelengths of the light emitted by the light emitters.

Figure 6:
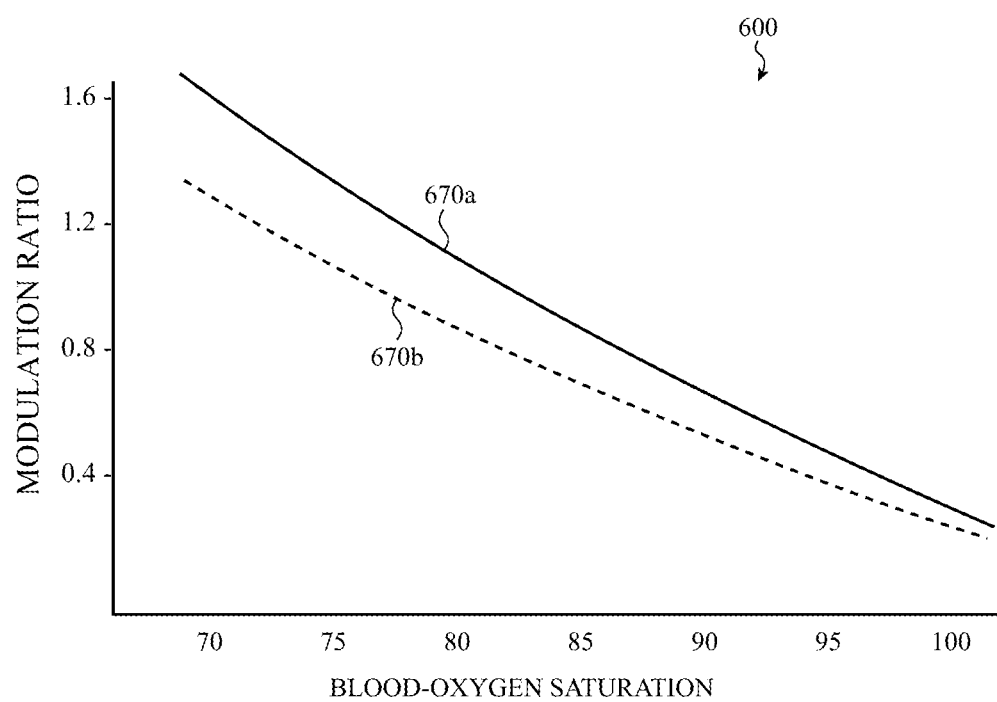
FIG. 6 illustrates two example calibration curves that correlate modulation ratios with estimated blood-oxygen saturation values for different wavelengths.

As noted above, in some cases, the measurement engine selects one or more calibration curves of a set of calibration curves based on the determined estimated wavelength(s). FIG. 6 illustrates two example calibration curves that correlate modulation ratios with estimated blood-oxygen saturation values for different wavelengths. The chart 600 in FIG. 6 shows two example calibration curves 670a and 670b. The calibration curve 670a may correspond to a first estimated wavelength or range of estimated wavelengths, and the calibration curve 670b may correspond to a second estimated wavelength or range of estimated wavelengths. For a given modulation ratio, each calibration curve 670a, 670b may provide an estimated blood-oxygen saturation value. As noted above, the calibration curves 670a, 670b may be determined during a calibration process in which wavelengths and true values for blood-oxygen saturation are known. A set of calibration curves may have any number of calibration curves corresponding to different estimated wavelengths and/or wavelength ranges.

Figure 7:
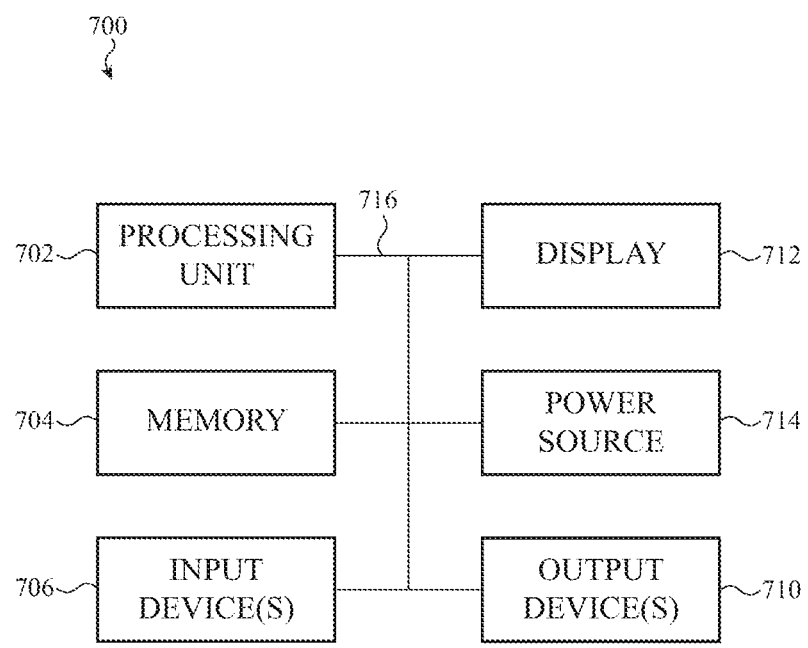
FIG. 7 is a sample electrical block diagram of an electronic device that may incorporate a sensing assembly as described herein.

FIG. 7 illustrates a sample electrical block diagram of an electronic device 700 that may incorporate a sensing assembly as described herein. The electronic device may in some cases take the form of any of the electronic devices described with reference to FIGS. 1-6, or other portable or wearable electronic devices. The electronic device 700 can include one or more of a display 712, a processing unit 702, a power source 714, a memory 704 or storage device, input devices 706 (e.g., light sensor(s)), and output devices 710 (a light emitter(s)).

The processing unit 702 can control some or all of the operations of the electronic device 700. The processing unit 702 can communicate, either directly or indirectly, with some or all of the components of the electronic device 700. For example, a system bus or other communication mechanism 716 can provide communication between the processing unit 702, the power source 714, the memory 704, the input device(s) 706, and the output device(s) 710.

The processing unit 702 can be implemented as any electronic device capable of processing, receiving, or transmitting data or instructions. For example, the processing unit 702 can be a microprocessor, a central processing unit (CPU), an application-specific integrated circuit (ASIC), a digital signal processor (DSP), or combinations of such devices. As described herein, the term "processing unit" is meant to encompass a single processor or processing unit, multiple processors, multiple processing units, or other suitably configured computing element or elements.

It should be noted that the components of the electronic device 700 can be controlled by multiple processing units. For example, select components of the electronic device 700 (e.g., an input device 706) may be controlled by a first processing unit and other components of the electronic device 700 (e.g., the display 712) may be controlled by a second processing unit, where the first and second processing units may or may not be in communication with each other. In some cases, the processing unit 702 may determine a biological parameter of a user of the electronic device, such as an ECG for the user.

The power source 714 can be implemented with any device capable of providing energy to the electronic device 700. For example, the power source 714 may be one or more batteries or rechargeable batteries. Additionally or alternatively, the power source 714 can be a power connector or power cord that connects the electronic device 700 to another power source, such as a wall outlet.

The memory 704 can store electronic data that can be used by the electronic device 700. For example, the memory 704 can store electrical data or content such as, for example, audio and video files, documents and applications, device settings and user preferences, timing signals, control signals, and data structures or databases. The memory 704 can be configured as any type of memory. By way of example only, the memory 704 can be implemented as random access memory, read-only memory, Flash memory, removable memory, other types of storage elements, or combinations of such devices.

In various embodiments, the display 712 provides a graphical output, for example associated with an operating system, user interface, and/or applications of the electronic device 700. In one embodiment, the display 712 includes one or more sensors and is configured as a touch-sensitive (e.g., single-touch, multi-touch) and/or force-sensitive display to receive inputs from a user. For example, the display 712 may be integrated with a touch sensor (e.g., a capacitive touch sensor) and/or a force sensor to provide a touch- and/or force-sensitive display. The display 712 is operably coupled to the processing unit 702 of the electronic device 700.

The display 712 can be implemented with any suitable technology, including, but not limited to liquid crystal display (LCD) technology, light emitting diode (LED) technology, organic light-emitting display (OLED) technology, organic electroluminescence (OEL) technology, or another type of display technology. In some cases, the display 712 is positioned beneath and viewable through a cover that forms at least a portion of an enclosure of the electronic device 700. In various embodiments, graphical outputs of the display 712 may be responsive to estimated blood-oxygen saturation values or other biological parameters determined by the device 700. For the processing unit 702 may cause the display 712 to display a notification or other graphical object(s) related to estimated blood-oxygen saturation values or other biological parameters.

In various embodiments, the input devices 706 may include any suitable components for detecting inputs. Examples of input devices 706 include light sensors, temperature sensors, audio sensors (e.g., microphones), optical or visual sensors (e.g., cameras, visible light sensors, or invisible light sensors), proximity sensors, touch sensors, force sensors, mechanical devices (e.g., crowns, switches, buttons, or keys), vibration sensors, orientation sensors, motion sensors (e.g., accelerometers or velocity sensors), location sensors (e.g., global positioning system (GPS) devices), thermal sensors, communication devices (e.g., wired or wireless communication devices), resistive sensors, magnetic sensors, electroactive polymers (EAPs), strain gauges, electrodes, and so on, or some combination thereof. Each input device 706 may be configured to detect one or more particular types of input and provide a signal (e.g., an input signal) corresponding to the detected input. The signal may be provided, for example, to the processing unit 702.

As discussed above, in some cases, the input device(s) 706 include a touch sensor (e.g., a capacitive touch sensor) integrated with the display 712 to provide a touch-sensitive display. Similarly, in some cases, the input device(s) 706 include a force sensor (e.g., a capacitive force sensor) integrated with the display 712 to provide a force-sensitive display.

The output devices 710 may include any suitable components for providing outputs. Examples of output devices 710 include light emitters, audio output devices (e.g., speakers), visual output devices (e.g., lights or displays), tactile output devices (e.g., haptic output devices), communication devices (e.g., wired or wireless communication devices), and so on, or some combination thereof. Each output device 710 may be configured to receive one or more signals (e.g., an output signal provided by the processing unit 702) and provide an output corresponding to the signal.

In some cases, input devices 706 and output devices 710 are implemented together as a single device. For example, an input/output device or port can transmit electronic signals via a communications network, such as a wireless and/or wired network connection. Examples of wireless and wired network connections include, but are not limited to, cellular, Wi-Fi, Bluetooth, IR, and Ethernet connections.

The processing unit 702 may be operably coupled to the input devices 706 and the output devices 710. The processing unit 702 may be adapted to exchange signals with the input devices 706 and the output devices 710. For example, the processing unit 702 may receive an input signal from an input device 706 that corresponds to an input detected by the input device 706. The processing unit 702 may interpret the received input signal to determine whether to provide and/or change one or more outputs in response to the input signal. The processing unit 702 may then send an output signal to one or more of the output devices 710, to provide and/or change outputs as appropriate.

The foregoing description, for purposes of explanation, uses specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings.

Although the disclosure above is described in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the some embodiments of the invention, whether or not such embodiments are described and whether or not such features are presented as being a part of a described embodiment. Thus, the breadth and scope of the present invention should not be limited by any of the above-described exemplary embodiments but is instead defined by the claims herein presented.

One may appreciate that although many embodiments are disclosed above, that the operations and steps presented with respect to methods and techniques described herein are meant as exemplary and accordingly are not exhaustive. One may further appreciate that alternate step order or fewer or additional operations may be required or desired for particular embodiments.

As used herein, the phrase "at least one of" preceding a series of items, with the term "and" or "or" to separate any of the items, modifies the list as a whole, rather than each member of the list. The phrase "at least one of" does not require selection of at least one of each item listed; rather, the phrase allows a meaning that includes at a minimum one of any of the items, and/or at a minimum one of any combination of the items, and/or at a minimum one of each of the items. By way of example, the phrases "at least one of A, B, and C" or "at least one of A, B, or C" each refer to only A, only B, or only C; any combination of A, B, and C; and/or one or more of each of A, B, and C. Similarly, it may be appreciated that an order of elements presented for a conjunctive or disjunctive list provided herein should not be construed as limiting the disclosure to only that order provided.

As described above, one aspect of the present technology is determining estimated blood-oxygen saturation values, and the like. The present disclosure contemplates that in some instances this gathered data may include personal information data that uniquely identifies or can be used to contact or locate a specific person. Such personal information data can include demographic data, location-based data, telephone numbers, email addresses, twitter IDs (or other social media aliases or handles), home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to provide haptic or audiovisual outputs that are tailored to the user. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act ("HIPAA"); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of determining spatial parameters, the present technology can be configured to allow users to select to "opt in" or "opt out" of participation in the collection of personal information data during registration for services or anytime thereafter. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data at a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, haptic outputs may be provided based on non-personal information data or a bare minimum amount of personal information, such as events or states at the device associated with a user, other non-personal information, or publicly available information.

What is claimed is:

1. A method for performing blood-oxygen saturation measurements using a wearable electronic device, the method comprising:
   emitting light toward a user using a light emitter positioned in the wearable electronic device;
   measuring a returned portion of the light from the user using one or more light sensors that are positioned in the wearable electronic device;
   sensing a temperature of the wearable electronic device using a temperature sensor that is positioned within the wearable electronic device;
   determining an estimated wavelength value for the emitted light using the sensed temperature and a drive current of the light emitter;
   selecting a calibration parameter from a set of calibration parameters using the estimated wavelength value; and
   determining, by a processor of the wearable electronic device, an estimated blood-oxygen saturation value based at least partially on the returned portion of the light and the calibration parameter.

2. The method of claim 1, wherein the light emitter is a first light emitter configured to emit first light at a first wavelength and the method further comprises:
   emitting second light at a second wavelength toward the user using a second light emitter positioned in the wearable electronic device;
   measuring a returned portion of the second light from the user using the one or more light sensors; and
   determining the estimated blood-oxygen saturation value based on the returned portion of the second light.

3. The method of claim 2 further comprising:
   determining a second estimated wavelength value for the second light using the sensed temperature and a drive current of the second light emitter;
   selecting a second calibration parameter from a set of calibration parameters using the second estimated wavelength value; and
   determining the estimated blood-oxygen saturation value using the second calibration parameter.

4. The method of claim 2, wherein:
   the first wavelength emitted by the first light emitter comprises red light; and
   the second wavelength emitted by the second light emitter comprises infrared light.

5. The method of claim 1, wherein determining the estimated wavelength comprises:
   determining a wavelength offset attributable to the drive current; and
   applying the wavelength offset to a nominal wavelength determined during a calibration process.

6. The method of claim 1, wherein the calibration parameter comprises a calibration curve that defines a relationship between a modulation ratio for the light and blood-oxygen saturation values.

7. The method of claim 6, wherein the calibration curve is determine using a calibration process in which the modulation ratio is determined using samples with known blood-oxygen saturation values.

8. The method of claim 1, further comprising determining:
   an estimated temperature of the light emitter using the sensed temperature; and
   determining the estimated wavelength based on the estimated temperature of the light emitter.

9. A method for performing a blood-oxygen saturation measurement using a wearable electronic device, comprising:
   emitting light at a first wavelength and a second wavelength using one or more light emitters the wearable electronic device;
   measuring a returned portion of the light that has interacted with a user using one or more light sensors;
   measuring a temperature using a temperature sensor of the wearable electronic device;
   determining a first estimated wavelength value for the first wavelength using the measured temperature and a drive current of the one or more light emitters;
   determining a second estimated wavelength value for the second wavelength using the measured temperature and the drive current of the one or more light emitters;
   selecting a calibration parameter from a set of calibration parameters using the first and second estimated wavelength values; and
   determining, by a processor of the wearable electronic device, an estimated blood-oxygen saturation value based at least partially on the returned portion of the light and the calibration parameter.

10. The method of claim 9, wherein determining the first estimated wavelength value comprises:
    determining a wavelength offset attributable to the drive current using a function generated during a calibration process of the wearable electronic device; and
    applying the wavelength offset to a nominal wavelength determined during the calibration process.

11. The method of claim 9, wherein:
    the light at the first wavelength is emitted by a first light emitter of the one or more light emitters; and
    the light at the second wavelength is emitted by a second light emitter of the one or more light emitters.

12. The method of claim 11, wherein:
    determining the first estimated wavelength value for the first wavelength comprises determining a first drive current for the first light emitter; and
    determining the second estimated wavelength value for the second wavelength comprises determining a second drive current for the second light emitter.

13. The method of claim 11, wherein:
    the light emitted at the first wavelength is red light; and
    the light emitted at the second wavelength is infrared light.

14. The method of claim 9, further comprising:
    determining an estimated temperature of the one or more light emitters using the measured temperature; and
    determining the first and second estimated wavelength values based on the estimated temperature.

15. A wearable electronic device comprising:
    an enclosure;

a measurement engine executing on a processing unit positioned in the enclosure;

a first light emitter positioned in the enclosure and configured to emit first light at a first wavelength;

a second light emitter positioned in the enclosure and configured to emit second light a second wavelength;

at least one light sensor positioned in the enclosure and configured to:
  sense a returned portion of the first and second light that has interacted with a user; and
  output a sensing signal to the measurement engine in response to sensing the returned portion of the first and second light; and a temperature sensor positioned in the enclosure and within a separate cavity from the first light emitter, the second light emitter and the at least one light sensor, the temperature sensor configured to:
  sense a temperature within the separate cavity of the enclosure; and
  output a temperature signal to the measurement engine, the temperature signal indicating the temperature, wherein:

the measurement engine is configured to:
  determine a modulation ratio of the first light emitted at the first wavelength to the second light emitted at the second wavelength;
  select a calibration parameter based on the sensed temperature; and
  determine an estimated blood-oxygen saturation value using the modulation ratio and the calibration parameter.

16. The wearable electronic device of claim 15, wherein the measurement engine is further configured to select the calibration parameter based on a first drive current of the first light emitter and a second drive current of the second light emitter.

17. The wearable electronic device of claim 16 wherein selecting the calibration parameter comprises:
  determining a first wavelength offset attributable to the first drive current using a function generated during a calibration process of the wearable electronic device; and
  determining a second wavelength offset attributable to the second drive current using the function generated during the calibration process of the wearable electronic device.

18. The wearable electronic device of claim 15, wherein:
  the light emitted at the first wavelength is red light; and
  the light emitted at the second wavelength is infrared light.

19. The wearable electronic device of claim 15, wherein:
  the wearable electronic device further comprises a display configured to provide a graphical output viewable along a first exterior surface of the enclosure;
  the enclosure comprises a cover defining a second exterior surface opposite first exterior surface; and
  the cover is configured to allow the light emitted by the first and second light emitters to pass through the cover.

20. The wearable electronic device of claim 15 wherein the calibration parameter comprises a calibration curve stored at the wearable electronic device and that defines a relationship between the modulation ratio and blood-oxygen saturation values.

* * * * *